United States Patent
Fernandez et al.

(10) Patent No.: US 7,333,201 B1
(45) Date of Patent: Feb. 19, 2008

(54) PROCESS AND APPARATUS FOR DETECTING THE APPROXIMATE LOCATION OF A COLOR SHIFT IN A TEXTILE MATERIAL

(76) Inventors: Conrad Layson Fernandez, 821 Brent Ln., Dalton, GA (US) 30720; Gary Lavere Munn, 608 Foster Rd., Dalton, GA (US) 30720; Thomas Jerry McClure, Jr., 4820 Shallow Creek Dr., Kennesaw, GA (US) 30144

( * ) Notice: Subject to any disclaimer, the term of this patent is extended or adjusted under 35 U.S.C. 154(b) by 53 days.

(21) Appl. No.: 11/357,763

(22) Filed: Feb. 17, 2006

(51) Int. Cl.
*G01J 3/46* (2006.01)
(52) U.S. Cl. ...................................... 356/402
(58) Field of Classification Search ............ None
See application file for complete search history.

(56) References Cited

U.S. PATENT DOCUMENTS

| | | | |
|---|---|---|---|
| 7,075,643 B2 * | 7/2006 | Holub | 356/326 |
| 2005/0008243 A1 * | 1/2005 | Fujino | 382/254 |
| 2006/0280360 A1 * | 12/2006 | Holub | 382/162 |

* cited by examiner

*Primary Examiner*—Tu T. Nguyen
(74) *Attorney, Agent, or Firm*—Needle & Rosenberg, P.C.

(57) ABSTRACT

Apparatus, methods, and textile materials created thereby or there from, in which the approximate location of a color shift along a run of textile material is determined. In one aspect, a plurality of color measure data points from the textile material is acquired and processed to determine color difference measures, which are compared to a predetermined threshold value in order to determine the approximate location of the color shift on the textile material.

20 Claims, 5 Drawing Sheets
(1 of 5 Drawing Sheet(s) Filed in Color)

FIG. 1
Exemplary Operating Environment

PROCESS AND APPARATUS FOR DETECTING THE APPROXIMATE LOCATION OF A COLOR SHIFT IN A TEXTILE MATERIAL

BACKGROUND OF THE INVENTION

During the production of textile fiber products, including carpeting, dye can be applied to the textile in order to produce a certain color. When changes or "shifts" in color occur, such as when a new color or colors are to be applied to a production run of carpet, it can be informative to know when the color shift has occurred. Typically, color shifts occur when the dye or dyes used to produce the old color or colors have been fully expended and the new dye or dyes used to produce the new color or colors have become introduced into the production process. A complete color shift is said to have occurred when the new color or colors are produced in a manner of predetermined uniformity. It can be informative to know where on the run of carpet that this shift has occurred so that a long run of carpet can be separated into sections of uniform color. In addition, waste can be reduced and non-uniform product can be removed.

SUMMARY

Embodiments of this invention provide a system or apparatus that is configured to determine approximately when and where a color shift has occurred in a textile material. An exemplary system or apparatus can comprise a camera for creating data points of color values on the textile material, a processing unit or computer for performing a statistical analysis and indicating the time of, and location, on the textile fiber, of the color shift. Additionally, in one aspect, a method of computing the location of a color shift on textile material is disclosed. Further, a textile material, such as, for example and not meant to be limiting, a carpet, created by the processes disclosed herein is disclosed.

Other systems, methods, features, and advantages of the color shift detection system will be or become apparent to one with skill in the art upon examination of the following figures and detailed description. It is intended that all such additional systems, methods, features, and advantages be included within this description, be within the scope of color shift detection system, and be protected by the accompanying claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

DETAILED DESCRIPTION OF THE INVENTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used in the specification and the appended claims, the singular forms "a," "an" and "the" include plural referents unless the context clearly dictates otherwise. Thus, for example, reference to "a textile" or "an additive" includes mixtures of two or more such textiles or additives, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, the terms "optional" or "optionally" mean that the subsequently described event or circumstance may or may not occur, and that the description includes instances where said event or circumstance occurs and instances where it does not.

"Textile" or "textiles", as used herein, means any structure made of raw textile materials and includes materials in both fibrous and sheet form. A textile material can comprise, for example, carpet.

"Carpet" and "carpet tile" are used herein in the manner as would be recognized by one of ordinary skill in the art and can include but are not limited to carpeting of a type such as cut pile, loops, and pattern loops, with widths of varying size including but not limited to about 8 to about 15 feet, dyeing categories including but not limited to solid shades and berbers (space dyed), and fiber type including, but not limited, to nylon and polyester, filament and staple, and various heatset and polymer type combinations.

"Color" as used herein means the different wavelengths of electromagnetic energy that produce visible light. Differing wavelengths produce different colors as seen by the human eye. Color can depend on the observer and the conditions in which the observation takes place. Color can be measured by physical or machine (non-human) methods using various techniques and standards as known by one of ordinary skill in the art.

Figure 5:
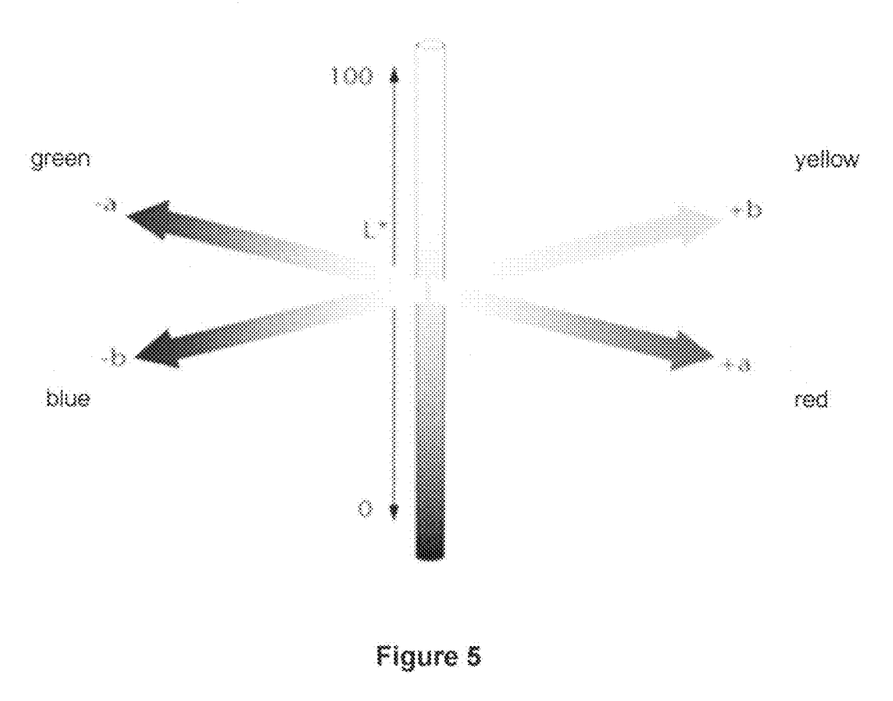
FIG. 5 is a schematic diagram showing CIELAB color space.

"CIELAB" as used herein means a color measurement method established by an organization called CIE (Commission Internationale de l'Eclairage). This standard is known by one of ordinary skill in the art. The values used by CIE are called $L^*$, $a^*$ and $b^*$. $L^*$ represents the difference between light (where $L^*=100$) and dark (where $L^*=0$). $A^*$ represents the difference between green ($-a^*$) and red ($+a^*$), and $b^*$ represents the difference between yellow ($+b^*$) and blue ($-b^*$). Using CIELAB any color corresponds to a place on the graph shown in FIG. 5. Variables of $L^*$, $a^*$, $b^*$ or $E^*$ are represented as delta $L^*$, delta $a^*$, delta $b^*$ or delta $E^*$, where delta $E^*=($delta $L^{*2}+$ delta $a^{*2}+$ delta $b^{*2})^{1/2}$. It represents the magnitude of the difference in color, but does not indicate the direction of the color difference. One skilled in the art will appreciate that there are other conventional color measurement methods as well which would be suitable for use in embodiments of the invention.

The present invention may be understood more readily by reference to the following detailed description of embodiments of the invention and the Examples included therein and to the Figures and their previous and following description.

Textiles

Generally, the disclosed processes and apparatuses can be used in connection with any textile known to those of skill in the art. In particular, the textile can have a front face and an opposed back face, and the textile can be progressively moved along a machine path, such as, for example, a path of a continuous dyeing and steaming apparatus.

In a further aspect, the disclosed processes and apparatuses can be used in connection with carpeting. For example, the textile can be broadloom carpeting, and the broadloom carpeting can be subsequently cut into carpet tiles. In a further aspect, the textile can be a carpet greige good, and the front face can comprise a carpet pile having a plurality of carpet fibers extending outwardly from the front face.

In one aspect, the carpet fibers can comprise any material suitable for carpet pile fibers known to those of skill in the art. In further aspects, the fibers can comprise polyamide, for example, nylon 6 or nylon 6,6; polyester; polyolefin, for example, polypropylene or polyethylene; polyacrylonitrile; wool; silk; cotton; or a copolymer thereof; or a mixture or blend thereof. In various aspects, the textile can be permeable.

In a further aspect, the fibers can have a length. For example, the length can be less than 0.5 inch, greater than about 0.5 inch, greater than about 1 inch, greater than about 1.5 inches, or greater than about 2 inches.

Color Shift

As part of the process of creating a textile, dye can be applied to the textile to create a particular color or pattern. Combinations of dyes of different colors can be used in order to create a particular color on the textile. During the manufacture of textile products, a manufacturing line can be used whereby long runs of textile material are processed in an assembly line fashion, traveling through various apparatus and processes used to create a finished product.

During that manufacturing process, long pieces of textile material can be joined together to allow for a fairly continuous operation of the manufacturing line without having to often stop the process to load new supplies of pre-processed textile materials. However, it may be desired to change the color of pieces of the run so that different color textile materials are produced during one long run of the manufacturing line. This change in color can be accomplished by altering the dyes that are applied to the textile material.

For the creation of various colors, one or more different dyes can be applied to textile material. This process is known to one of ordinary skill in the art, and is not unlike the mixing of primary or other colors to create a different color. During the color change over process, when new dyes begin to be emitted from the dye dispensing apparatus on to the textile material, a certain length of the textile material will contain a change in color from the old color to the new desired color. This change in color is called a color shift.

At a point during the run, the color change will stabilize or reach the desired color. Once this change occurs to the desired color, a color shift is said to have taken place. The manufacturer of the textile material can if desired, once certain processing steps are completed, cut off or segment a long run of textile material into pieces based on color. For example, in the case of carpets, an initial segment of color X can be created and then later in the same run, the process can switch to producing color Y. The carpet manufacturer can cut or separate the run into two pieces so that a roll of carpet of color X is created and a roll of carpet of color Y is created. The separation can take place in the region approximate to the color shift in order to create two rolls with a minimal amount of waste.

Determination of the approximate location of the completed color shift can take place by visual human inspection. However, it is also possible to use embodiments of the invention to automate the process of determining the approximate location of the color shift. Further embodiments of the invention provide for apparatus that automate the process of approximately locating the color shift. Further embodiments of the invention comprise a textile material created using the processes described herein.

Exemplary Color Measurement Methodologies

The automated determination of the location of the color shift can use a color measurement method to physically quantify color at various sample points on the textile material. Such color measurement methodologies include, but are not limited to CIELUV, CIELAB, Munsell, NCS, and Ostwald. The color measurement methodology allows for acquisition, storage, and manipulation of color measure data points; that is, data points along the textile material where an apparatus for measuring color acquires a color measurement for that location. The color measurement methodology allows for the manipulation of color measure data points in a computer or other similar type of arithmetic processing unit. Comparisons of various data points and statistical calculations can take place, using numerical representations of color.

The acquisition of a color measure data point can be done using various electromechanical and electrical devices. In one aspect, these devices include various types of readers or cameras implementing various technologies and can be divided into categories such as reflectance spectrophotometers and calorimeters. In another aspect, the camera can use charge coupled devices (CCD's).

Conventional reflectance spectrophotometers measure the amount of light reflected by a surface as a function of wavelength to produce a reflectance spectrum. The operation of a spectrophotometer is basically to illuminate the sample with white light and to calculate the amount of light that is reflected by the sample at each wavelength interval. Typically, this can be done by passing the reflected light through a monochromating device that splits the light up into separate wavelength intervals.

Conventional colorimeters measure tristimulus values (values of the three primary colors) and can operate using three broad-band filters. Consequently, calorimeters may not provide spectral reflectance data but can have a low cost of manufacture and portability.

The color measuring device may require the use of an external illumination source, or light, in order to capture color measure data points. One of ordinary skill in the art would appreciate that conventional, suitable illumination devices, such as, for example, but not limited to LED lighting, fluorescent lighting, and the like. In one aspect, the illumination source is configured to produce an even power distribution through out the visible spectrum, or as close to even as is known to one of ordinary skill in the art.

In one aspect, the color measuring device is configured for interfacing with a computer or similar device such as a microcontroller or other arithmetic processing unit. In another aspect, the color measuring device can generate an electronic stream of data in a format that conveys color information using a chosen color measurement methodology. In a further aspect, the color measuring device can be controlled by the computer or similar device. For example, the timing or frequency of the data acquisition can be controlled.

In one aspect, the color measuring device can acquire color measure data points at any stage of the manufacturing process including while the textile material is moving along the machine path in the manufacturing line. In this aspect, the color measuring device can be capable of acquiring adequate numbers of data points while the textile material moves at speeds from greater than 0 to about 175 fpm or more. In another aspect, the color measuring device can be mounted at a suitable location along the manufacturing process so that data points can be acquired in a sufficient number to enable the calculation of the location of the color shift. In one exemplary aspect, the color measuring device can be located after a process on a manufacturing line that produces a wet textile material, such as a location where the temperature and water content is stable and/or consistent. Typically, this would occur at a location on the manufacturing line downsteam of a steamer and/or an extractor process section. This location can limit the impact on thermo-chromatic effects or moisture variation.

In another aspect, associated with the acquisition of the data points, the present invention can comprise an indication of where, in a linear distance sense, the data point was acquired on the run of textile material. In another aspect, a distance measuring device can be coupled to the system to provide additional information to the computer or similar device so that each data point also has a distance value associated with it. Thus, in operation, the approximate location of the color shift, which is computed from the data points, can be determined.

In a further aspect, data and calculations can be stored in a computer or similar device. Such devices are described herein.

In one aspect, to identify when a color shift has occurred, comparisons to reference colors are used. In an alternative aspect, comparisons to color or colors on the textile material can be used. One exemplary method is to calculate an average or central tendency for a run or portion of a run of textile material. Then using that calculated average, a comparison to individual color measure data points can be done, which creates a color difference measure between an individual data point and the calculated average. A further comparison can then be done between the determined color measure difference to a predetermined threshold value, and, when the color measure difference is less than or equal to the predetermined threshold value, the color shift can be deemed to have been completed.

In one aspect, the average can be computed via known methods for calculating a central tendency, which includes, for example, computing an arithmetic mean. Of course, it is contemplated that other methods for computing an average can be used as well, such as, for example and not meant to be limiting, computation of the median, the mode, the geometric mean, the harmonic mean, the generalized mean, a weighted mean, a truncated mean, an interquartile mean, a trimean, a trimedian, and a normalized mean. In one example, an average metric can be created using a generic formula:

$$Y = f^{-1}((f(x1) + f(x2) + \ldots + f(xn))/n),$$

where f is any invertible function. For example, expmean (exponential mean) is a mean using the function $f(x) = e^x$ and due to its nature, it is biased towards the higher values.

In another exemplary aspect, a method for calculating a purified average comprises: calculating the mean and standard deviation for the plurality of color measure data points; and calculating the average (via one of the methods discussed above, including an arithmetic mean) of the color measure data points that are within about ±3 standard deviation of the mean, wherein that calculated average is the purified average. In a further exemplary aspect, a method for calculating a purified average comprises: calculating the standard deviation of all the measure color data points; discarding any data points that are outside ±3 standard deviation of the mean; recalculating the standard deviation for the reduced number of data points and discarding any data points that fall outside ±3 standard deviation; repeating the previous step until there are no data points outside ±3 standard deviation; and calculating the mean of these remaining points. The resultant calculated mean is the purified average.

It will be appreciated that calculation of the color difference measure can be done using methods known to a person of ordinary skill in the art. Exemplary methods are discussed below.

CIELAB color space provides a three-dimensional representation for the perception of color stimuli. If two points in space, representing two stimuli, are coincident then the color difference between the two stimuli is zero. As the distance in space between two points ($L_1^*$, $a_1^*$, $b_1^*$ and $L_2^*$, $a_2^*$, $b_2^*$) increases, it is reasonable to assume that the perceived color difference between the stimuli that the two points represented increases accordingly. One measure of the difference in color between two stimuli is, therefore, the Euclidean distance DE* between the two points in the three-dimensional space.

Delta Ecmc (DEcmc or DeCMC) was developed by the Color Measurement Committee of the Society of Dyes and Colourists in Great Britain. DEcmc is an ellipse-based equation for computing DE values as an alternative to the rectangular coordinates of the CIE L*a*b* color space. DEcmc may more closely matches human vision when judging the acceptability of color difference.

The CMC color difference formula allows calculation of tolerance ellipsoids around the target standard where the dimensions of the ellipsoid are a function of the position in color space of the target. The design of this formula allows for two user-definable coefficients 1 and c and the formula is thus normally specified as CMC(1:c). The values of 1 and c modify the relative importance that is given to differences in lightness and chroma respectively. The CMC(2:1) version of the formula has been shown to be useful for the estimation of the acceptability of color difference evaluations. The CMC(2:1) equation is a British Standard (BS:6923) for the assessment of small color differences and is currently being considered as an ISO standard.

In one aspect, a predetermined threshold value can be established to use as a comparison to the computed color difference measure. For example, the predetermined threshold value for DEcmc(2:1), can be about 0.5 for a textile material. In one exemplary aspect, predetermined threshold values can be calculated by taking offline spectrophotomer measurements of processed textile materials and obtaining data for use in computing an appropriate predetermined threshold value. Other predetermined threshold values, appropriate for the color difference calculation used, are know to those skilled in the art.

In a further aspect of the present invention, comparison of the color difference measure for each color measure data point is made to the predetermined threshold value (either compared one at a time until the predetermined threshold value is reached or computed for each data point). In one aspect, if the color difference measure for a point (the ith point) is equal to or less than the threshold value, then the color shift is said to have taken place at the ith point, which is the point where the threshold value was met.

The ith point has a linear distance along the textile material associated with it. Therefore, the location of the color shift can be indicated to have taken place by reporting the location of the ith data point where the threshold value was met.

Optionally, other requirements can be implemented to determine the data point that indicates the color shift. For example, an algorithm can be used that waits until j consecutive data points were at or below the threshold, where j could be 2 or more.

In another aspect of the present invention, an indication can be given to operators of the textile material manufacturing line upon determination of the color shift location. For example, a computer display could be used whereby a numerical distance from a certain point indication is given to the operator. Of course, it is contemplated that other types of displays can be used such as, for example, LED or LCD displays driven by appropriate electronics.

In an exemplary aspect, an operator of the manufacturing line can use the location of the color shift information to determine where to segment or cut the run of textile material, which results in rolls of textile material of the same color. In this context, "same" means a color consistency of a certain grade and not necessarily indicating a physical exactness of color throughout the roll.

Figure 1:
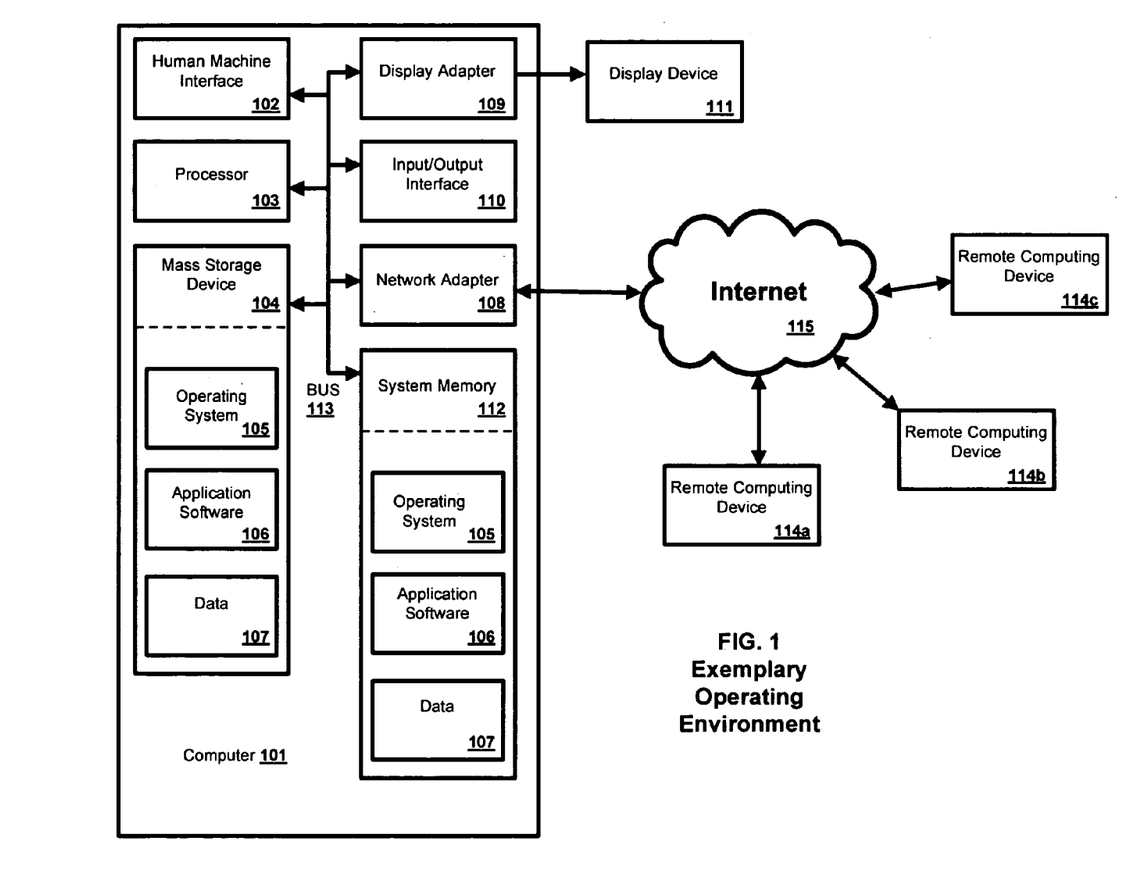
FIG. 1 is an exemplary operating environment for performing embodiments of the invention.

Turning now to the figures, FIG. 1 is a block diagram illustrating an exemplary operating environment for performing an exemplary embodiment of the method of the present invention. One will appreciate that this exemplary operating environment is only meant as an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

In one aspect, the method can be operational with numerous other general purpose or special purpose computing system environments or configurations Examples of well known computing systems, environments, and/or configurations that may be suitable for use with the system and method include, but are not limited to, personal computers, server computers, laptop devices, and multiprocessor systems. Additional examples include set top boxes, programmable consumer electronics, network PCs, minicomputers, mainframe computers, distributed computing environments that include any of the above systems or devices, and the like.

In another aspect, the method may be described in the general context of computer instructions, such as program modules, being executed by a computer. Generally, program modules include routines, programs, objects, components, data structures, etc, that perform particular tasks or implement particular abstract data types. In a further aspect, the system and method may also be practiced in distributed computing environments where tasks are performed by remote processing devices that are linked through a communications network. In a distributed computing environment, program modules may be located in both local and remote computer storage media including memory storage devices.

In a further aspect, the method disclosed herein can be implemented via a general-purpose computing device in the form of a computer 101. The components of the computer 101 can include, but are not limited to, one or more processors or processing units 103, a system memory 112, and a system bus 113 that couples various system components including the processor 103 to the system memory 112.

In one aspect, the system bus 113 represents one or more of several possible types of bus structures, including a memory bus or memory controller, a peripheral bus, an accelerated graphics port, and a processor or local bus using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. This bus, and all buses specified in this description can also be implemented over a wired or wireless network connection. In exemplary aspects, the bus 113, and all buses specified in this description can also be implemented over a wired or wireless network connection and each of the subsystems, including the processor 103, a mass storage device 104, an operating system 105, application software 106, data 107, a network adapter 108, system memory 112, an Input/Output Interface 110, a display adapter 109, a display device 111, and a human machine interface 102, can be contained within one or more remote computing devices 114 a,b,c at physically separate locations, connected through buses of this form, which, in effect, implements a fully distributed system.

In one aspect, the computer 101 typically includes a variety of computer readable media. Such media can be any available conventional media that is accessible by the computer 101 and includes both volatile and non-volatile media, removable and non-removable media. In a further aspect, the system memory 112 includes computer readable media in the form of volatile memory, such as random access memory (RAM), and/or non-volatile memory, such as read only memory (ROM). In another aspect, the system memory 112 typically contains data such as data 107 and/or program modules such as operating system 105 and application software 106 that are immediately accessible to and/or are presently operated on by the processing unit 103.

In a further aspect of the invention, the computer 101 may also include other removable/non-removable, volatile/non-volatile computer storage media. By way of example, FIG. 1 illustrates a mass storage device 104 which can provide non-volatile storage of computer code, computer readable instructions, data structures, program modules, and other data for the computer 101. For example and not meant to be limiting, a mass storage device 104 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

It is further contemplated that any number of program modules can be stored on the mass storage device 104, including by way of example, an operating system 105 and application software 106. One skilled in the art will appreciate that both the operating system 105 and application software 106 (or some combination thereof) may include elements of the programming and the application software 106. Data 107 can also be stored on the mass storage device 104. In another aspect, data 107 can be stored in any of one or more databases known in the art. Examples of such databases include, DB2®, Microsoft® Access, Microsoft® SQL Server, Oracle®, mySQL, PostgreSQL, and the like. In other exemplary aspects, the databases can be centralized or distributed across multiple systems.

In a further aspect, a user can enter commands and information into the computer 101 via an input device (not shown). Examples of such input devices include, but are not limited to, a keyboard, pointing device (e.g., a "mouse"), a microphone, a joystick, a serial port, a scanner, and the like. These and other input devices can be connected to the processing unit 103 via a human machine interface 102 that is coupled to the system bus 113, but may be connected by other interface and bus structures, such as a parallel port, game port, or a universal serial bus (USB).

The network adapter can be connected to a LAN wherein the computer 101 communicates with other devices connected to the LAN as well, such as the color measuring device.

In a further aspect, a display device 111 can also be connected to the system bus 113 via an interface, such as a display adapter 109. For example, a display device can be a monitor or an LCD (Liquid Crystal Display). In addition to the display device 111, other output peripheral devices can comprise components such as speakers (not shown) and a printer (not shown) which can be connected to the computer 101 via the Input/Output Interface 110.

It is contemplated that the computer 101 can operate in a networked environment using logical connections to one or more remote computing devices 114 a,b,c By way of example, a remote computing device can be a personal computer, portable computer, a server, a router, a network computer, a peer device or other common network node, and so on. Logical connections between the computer 101 and a remote computing device 114 a,b,c can be made via a local area network (LAN) and a general wide area network (WAN). Such network connections can be through a network adapter 108. A network adapter 108 can be implemented in both wired and wireless environments. Such networking environments are commonplace in offices, enterprise-wide computer networks, intranets, and the Internet 115.

For purposes of illustration, application programs and other executable program components such as the operating system 105 are illustrated herein as discrete blocks, although it is recognized that such programs and components reside at various times in different storage components of the computing device 101, and are executed by the data processor(s) of the computer. An implementation of application software 106 may be stored on or transmitted across some form of computer readable media. Computer readable media can be any available media that can be accessed by a computer. By way of example, and not limitation, computer readable media may comprise "computer storage media" and "communications media." "Computer storage media" include volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The processing of the disclosed method can be performed by software components. The disclosed method may be described in the general context of computer-executable instructions, such as program modules, being executed by one or more computers or other devices. Generally, program modules include computer code, routines, programs, objects, components, data structures, etc. that performs particular tasks or implements particular abstract data types. The disclosed method may also be practiced in grid-based and distributed computing environments where tasks are performed by remote processing devices that are linked through a communications network. In a distributed computing environment, program modules may be located in both local and remote computer storage media including memory storage devices.

Figure 2:
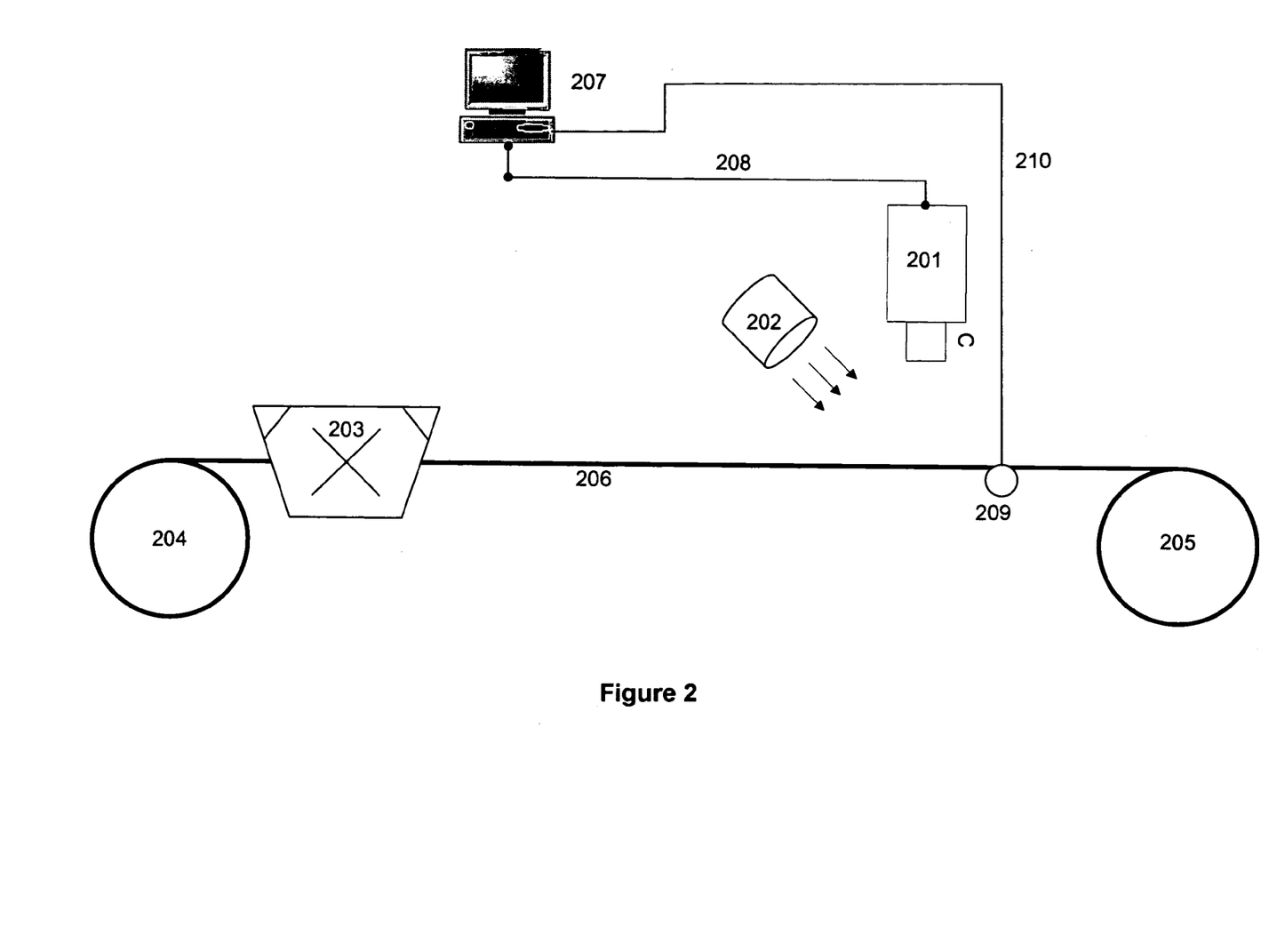
FIG. 2 is a schematic diagram of an exemplary embodiment of the invention in use on a simplified manufacturing line.

FIG. 2 shows a schematic diagram of an exemplary embodiment of the invention. For example, a camera 201 is used to acquire color measure data points from the run of textile materials 206. The camera 201 can be, for example, a SpectroCam distributed by the DVT Corporation. The camera 201 is connected to a computer 207 via electrical connection 208. This connection can be a serial cable, a USB connection, network cable in a LAN, a wireless connection, or other connections known to one skilled in the art. A light source 202 provides illumination for the camera 201. The light source can be mounted so it provides appropriate illumination for the camera. The textile material 206 is shown on a manufacturing line with rollers or other dispensers 204 and 205 and a dying process 203 where color is applied to the textile material 206. The footage indicator 209 provides a distance reference to the computer 207 via an electrical connection whereby a data point has an associated linear distance measure associated with it.

Figure 3:
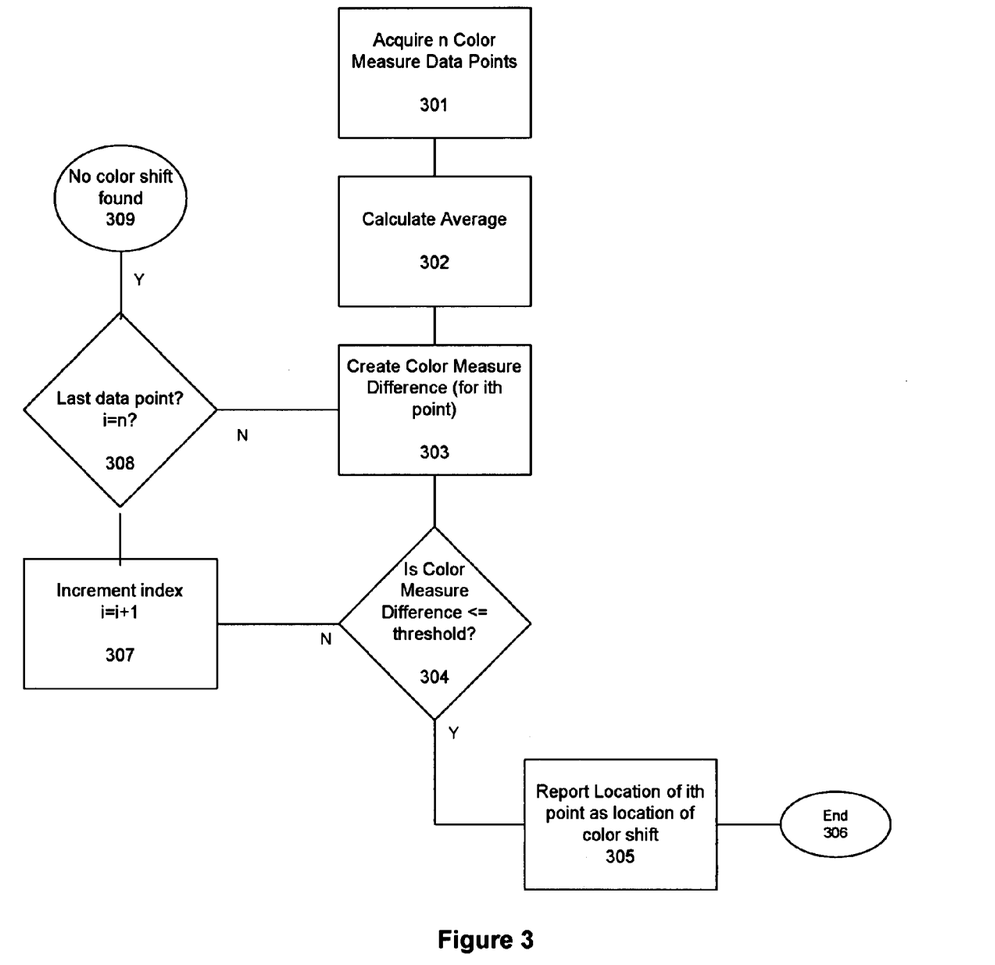
FIG. 3 is a flowchart diagram showing the steps of a process embodiment of the invention.

FIG. 3 is a flowchart showing an embodiment of the invention comprising a process for determining the color shift location. In block 301, a plurality of color measure data points are obtained. The number of data points is n. An index pointer, i, can be used such that i=1 to n. These data points can be obtained via means set forth herein, including but not limited to spectrophotometers and calorimeters. The data points can be stored in a computer or similar device. The number of data points, n, can be selected by the user. In one aspect, the number of data points can be about 1000. In another aspect, the sampling rate can be about 200 msec. In block 302, an average color value for the n color measure data points is computed. This computation can take place in and be stored in a computer or similar device. The average color value, also known as the central tendency, can be calculated using methodologies described herein.

In block 303, an index, i, can be used to point to a single color measure data point acquired in block 301. Initially, i can be set to 1. In block 303, a color difference measure is computed using the average created in block 302 and the ith data point. Calculation of the color difference measure in block 303 can be done using various methods described herein.

Optionally, this color difference measure can be created for all i=1 to n data points. Optionally, i can be set to some other starting color measure data point, with appropriate adjustments made to the loop checking portions of the algorithm, with said adjustments being known to one of ordinary skill in the art.

The color difference measure for the ith data point is compared to a predetermined threshold value in block 304. This threshold value can be chosen as described herein. If the ith color measure data point has a color difference measure of equal to or less than the predetermined threshold value, then the Yes path from block 304 to block 305 is followed. In block 305, the location of the ith data point in relation to a distance along the textile material is looked up and reported out as the approximate location of the color shift. The process ends at block 306.

If the ith color measure data point has a color difference measure of greater than the predetermined threshold value, then the No path from block 304 to block 307 is followed. In block 307, the index counter, i, is incremented by one. In block 308, if the index counter, i, is not equal to n (the total number of data points), the process loops back to block 303 along the No path. If the index counter is equal to n (i=n), the process goes to block 309 and reports that all color measure data points have been examined and no color shift was found, and the process ends.

EXAMPLE

Figure 4:
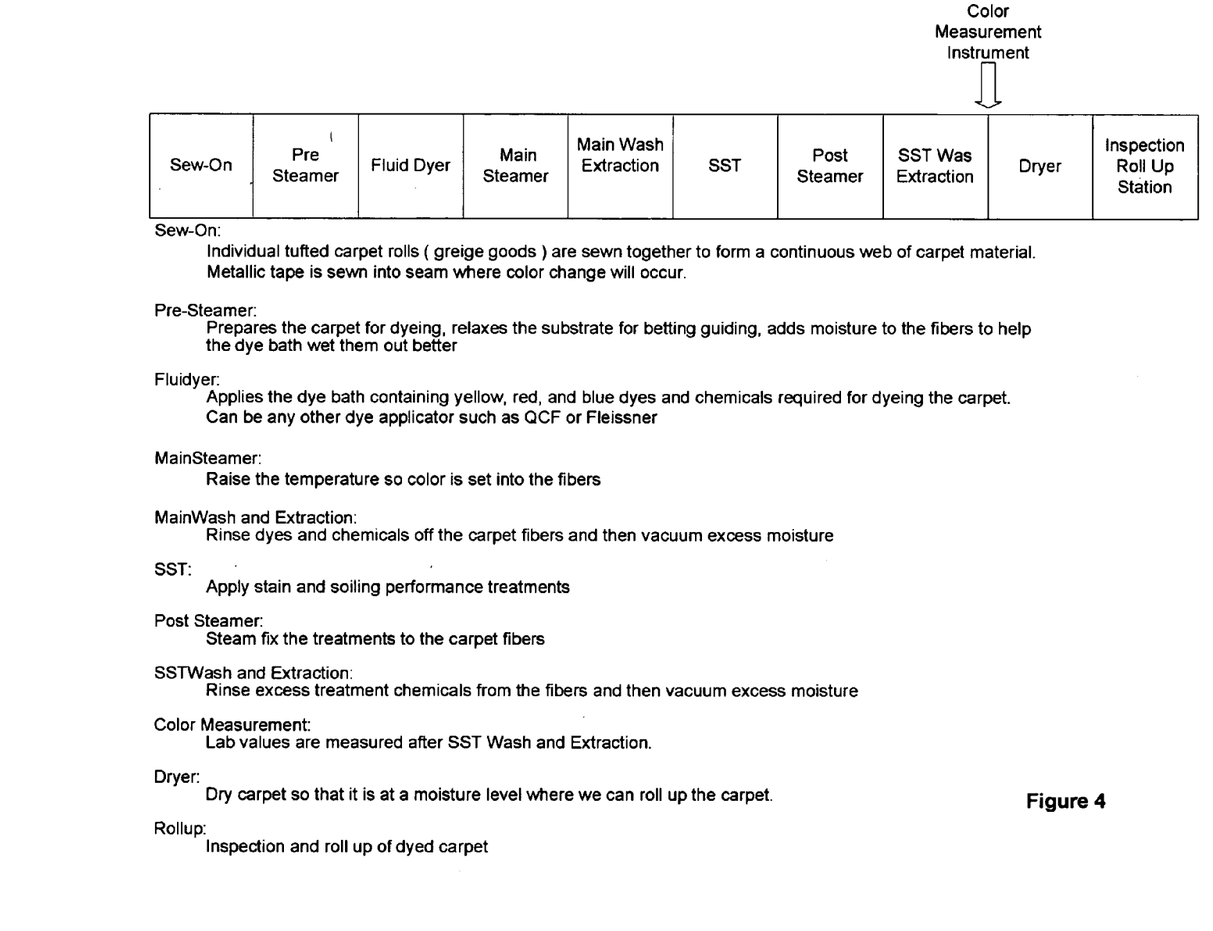
FIG. 4 is a schematic diagram of an exemplary carpet manufacturing line where embodiments of the invention can be used.

The use of an embodiment of the invention is shown in FIG. 4, a diagram of a carpet manufacturing line called Kuster. Kuster dyeing can involve running the carpet along a conveyer belt under a row of jets that apply computer controlled color. The various process stations for the manufacturing line are described as follows:

PreSteamer—prepares the carpet for dyeing, relaxes the substrate for betting guiding, adds moisture to the fibers to help the dyebath wet them out better;

Fluid Dyer or other dye applicator (such as QCF or Fleissner)—applies the dyebath containing yellow, red, and blue dyes and chemicals required for dyeing the carpet;

MainSteamer—raises the temperature so color is set into the fibers;

MainWash and Extraction—rinses dyes and chemicals off the carpet fibers and then vacuums excess moisture;

SST—applies stain and soiling performance treatments;

Post Steamer—steam fixes the treatments to the carpet fibers,

SSTWash and Extraction—rinses excess treatment chemicals from the fibers and then vacuum excess moisture Dryer—dries the carpet so that it is at moisture level where the carpet can be rolled up; and Rollup—inspection and roll up of dyed carpet;

An exemplary embodiment of the invention, as used in the Kuster manufacturing line, is described below. The DVT camera is located a certain distance in front of the Roll Up station, after an extractor section of the process. The camera can be mounted in a housing to minimize extraneous influences and to provide physical protection. A light source can be mounted in proximity to the camera so that the area of color measurement is illuminated. In one example, a Gretag MacBeth Sol Source D65 Light with D65 filter and Cooper Lighting Lumiere Hollywood ultra-compact projector light source can be used. When a seam (a seam being a location where continues pieces of textile material, namely carpet, have been joined together) reaches the DVT, the footage count is reset and a signal is sent to a reporting/analysis service telling it to perform analysis on the recently completed roll. This is the analysis on the entire roll versus just the color changeover section.

The color data following the seam is on the new color along with the transition to the new color. The DVT software (that is, software to implement the process and accept the data information) waits for the seam to reach the Roll Up station. When the elapsed footage is greater than or equal to the distance from DVT to Roll Up, the signal is sent to the reporting/analysis service telling it to perform the cut off calculation for this new color.

Footage is measured using an encoder mounted to a driven roller so that slippage may not affect the length measurements. In one example, a Red Lion encoder model number 4610120 which provides 120 pulses per encoder revolution can be used. These pulses are fed into a high speed counting device and scaled to the corresponding length. The encoder can be directly coupled to a driven roller or a wheel can be mounted on the shaft of the encoder so it is in contact with the driven roller and rotates with the roller.

To synchronize the footage for each color run, zero or clear the footage when a seam is detected. For example, seam detection can be performed by an array of Turck sensors, such as, for example, model Ni60-K90SR-FZ3×2/F2 or model Ni60-K90SR-FZ3×2. In one aspect, alternate sensors of differing frequencies can be used so that adjacent sensors do not affect each other.

Cut off calculation is based on the color measurements from the seam of the new color to the distance from DVT to Roll Up. This portion of the entire color run can be used for calculating the average color of the run (Average L,a,b). The average color can be a purified average. All of the data points are used to calculate the sigma values (standard deviation) for L, a, and b. Upper control and lower control limits are set to +3sigma and −3sigma respectively. Points outside these control limits are not used to calculate this purified average. This process is repeated until all points are inside the ±3 sigma control limits. From this data set, the +average color (average L,a,b) can be calculated.

From this average color, a color difference (DeCMC) profile is created using a (2:1) ratio. Using all of the original data points, the color difference (DeCMC) of each point with respect to the color average is calculated. The original points are ordered by footage. So starting at zero footage (typically at the seam location), the DeCMC is compared to a threshold (0.5). If the DeCMC is greater than or equal to the predetermined threshold value, the system proceeds to the next color data/footage point and continues evaluating the DeCMC of each point. When the DeCMC drops below the predetermined threshold value, the footage of this color data point is recorded as the cut off location. This footage is where the color has stabilized to the new color, or in other words, the color shift has occurred. The Roll Up operator cuts out the material from the seam to this footage and throws away as waste.

Outside of this logic, running in the background, the data archiving software continuously stores footage and color (L,a,b) data every 200 milliseconds. Note that the longer the distance from the DVT to the Roll Up station, the more data points to use for the color average calculation.

The preceding description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. The corresponding structures, materials, acts, and equivalents of all means or step plus function elements in the claims below are intended to include any structure, material, or acts for performing the functions in combination with other claimed elements as specifically claimed.

Accordingly, those who work in the art will recognize that many modifications and adaptations to the present invention are possible and can even be desirable in certain circumstances and are a part of the present invention. Other embodiments of the invention will be apparent to those skilled in the art from consideration of the specification and practice of the invention disclosed herein. Thus, the preceding description is provided as illustrative of the principles of the present invention and not in limitation thereof. It is intended that the specification and examples be considered as exemplary only, with a true scope and spirit of the invention being indicated by the following claims.

REFERENCES

1. Aspland, Richard and Shanbhag, Pramod, "Comparison of Color-Difference Equations for Textiles": CMC(2:1) and CIEDE2000, AATCC Review, pp. 26-30, June 2004.
2. Berns, R. S. (2000). Billmeyer and Saltzman's Principals of Color Technology (3rd ed.). New York: John Wiley and Sons, Inc., pp. 117-118.

What is claimed is:

1. A process for identifying a color shift on a length of textile material wherein the color shift is associated with a predetermined threshold value, comprising:
    acquiring a plurality of color measure data points from the length of textile material wherein a change in color applied to the textile material occurs at some location on the textile material;
    associating each color measure data point with a location on the textile material from which the color measure data point was acquired;
    calculating an average of the acquired plurality of color measure data points;
    computing a color difference measure for each color measure data point by incrementally comparing the respective color measure data point to the calculated average; and
    comparing the color difference measure to the predetermined threshold value, wherein the first color measure data point to have a color difference measure of equal to or less than the predetermined threshold value is identified as the approximate location of the color shift.

2. The process of claim 1, wherein the color measure data points comprise a CIELAB color representation.

3. The process of claim 2, wherein the color difference measure is calculated using a DeCMC equation.

4. The process of claim 3, wherein the color difference measure is calculated using a DeCMC(2:1) equation.

5. The process of claim 4, wherein the threshold value is about 0.5.

6. The process of claim 1, wherein the textile material is a carpet.

7. The process of claim 1, wherein the average of the acquired plurality of color measure data points is a purified average determined by:
    calculating the mean and standard deviation for the plurality of color measure data points;
    removing from the plurality of color measure data points all points that fall outside of about ±3 standard deviation of the mean and repeating this step until all data points fall within about ±3 standard deviation of the mean of the remaining color measure data points; and
    calculating the average of the remaining color measure data points wherein that average is the purified average.

8. The process of claim 1, further comprising steaming the textile material prior to the acquiring step.

9. The process of claim 1, further comprising extracting the textile material prior to the acquiring step.

10. An apparatus for identifying a color shift on a length of textile material wherein the color shift is associated with a predetermined threshold value, comprising:
    a camera configured for acquiring from the length of textile material plurality of color measure data points;
    a location indicator configured for associating a color measure data point with a location on the length of textile material from which the color measure data point was acquired;

a processing unit comprising:
  a memory storage device coupled to the camera and the location indicator and configured for receiving and storing the color measure data points; and
  a program module, stored in the memory storage device, which provides instructions to the processing unit, which responsive to the instructions of the program module, cause the processing unit to:
    calculate an average of the color measure data points;
    compare, incrementally, one or more color measure data point to the calculated average, wherein a color difference measure is computed for the respective color measure data point; and
    compare the color difference measure to a threshold value, wherein the first color measure data point to have a color difference measure of equal to or less than the threshold value is identified as the approximate location of the color shift.

11. The apparatus of claim 10, wherein the camera produces color measure data points comprising CIELAB color representations.

12. The apparatus of claim 10, wherein the textile material is carpet.

13. The apparatus of claim 10, wherein the camera is a spectrophotometer.

14. The apparatus of claim 10, wherein the camera is a colorimeter.

15. The apparatus of claim 10, wherein the camera is positioned downstream from a steamer for the textile material.

16. The apparatus of claim 10, wherein the camera is positioned downstream from an extractor for the textile material.

17. A textile material created by a process, comprising:
  acquiring a plurality of color measure data points from a length of textile material, wherein a change in color applied to the textile material occurs at least one location on the textile material;
  associating each color measure data point with a location on the textile material from which the color measure data point was acquired;
  calculating an average of the acquired plurality of color measure data points;
  incrementally comparing each respective color measure data point to the calculated average to determine a color difference measure for each respective color measure; and
  comparing the color difference measure to a predetermined threshold value wherein the first color measure data point to have a color difference measure of equal to or less than the predetermined threshold value is identified as the approximate location of the color shift.

18. The textile material of claim 17, wherein the textile material is a carpet.

19. The textile material of claim 18, wherein the color measure data points are acquired after a steamer or extractor process on a textile material manufacturing line.

20. The textile material of claim 17, wherein the average of the acquired plurality of color measure data points is a purified average determined by:
  a. calculating the mean and standard deviation for the plurality of color measure data points;
  b. removing from the plurality of color measure data points all points that fall outside of about ±3 standard deviation of the mean
  c. repeating step b until all data points fall within about ±3 standard deviation of the mean of the remaining color measure data points; and
  d. calculating the average of the remaining color measure data points, wherein that calculated average is the purified average.

* * * * *